(12) United States Patent
 Black

(10) Patent No.: US 9,687,441 B1
(45) Date of Patent: Jun. 27, 2017

(54) COMPOSITIONS FOR USE WITH A FASCIA TISSUE TREATMENT DEVICE TO REDUCE CELLULITE

(71) Applicant: Ashley Diana Black International Holdings, LLC, Pearland, TX (US)

(72) Inventor: Ashley D. Black, Pearland, TX (US)

(73) Assignee: Ashley Diana Black International Holdings, LLC, Pearland, TX (US)

( * ) Notice: Subject to any disclaimer, the term of this patent is extended or adjusted under 35 U.S.C. 154(b) by 0 days.

(21) Appl. No.: 15/182,239

(22) Filed: Jun. 14, 2016

(51) Int. Cl.
| | | |
|---|---|---|
| *A61K 36/00* | (2006.01) | |
| *A61K 8/99* | (2017.01) | |
| *A61Q 19/06* | (2006.01) | |
| *A61K 8/97* | (2017.01) | |
| *A61K 8/37* | (2006.01) | |
| *A61K 8/49* | (2006.01) | |
| *A61K 8/34* | (2006.01) | |

(52) U.S. Cl.
CPC ............... *A61K 8/99* (2013.01); *A61K 8/34* (2013.01); *A61K 8/345* (2013.01); *A61K 8/37* (2013.01); *A61K 8/498* (2013.01); *A61K 8/97* (2013.01); *A61Q 19/06* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 7,906,496 | B2 * | 3/2011 | Beumer | A61K 8/37 514/167 |
| 2002/0197289 | A1 * | 12/2002 | Chevalier | A61K 8/027 424/401 |
| 2007/0116696 | A1 * | 5/2007 | Riley | A61K 8/97 424/94.5 |
| 2011/0305737 | A1 * | 12/2011 | Alexiades-Armenakas | A61K 8/922 424/401 |

FOREIGN PATENT DOCUMENTS

| | | | | |
|---|---|---|---|---|
| FR | 2958848 | A1 * | 10/2011 | ............... A61K 8/97 |
| RU | 2262919 | C1 * | 10/2005 | |

* cited by examiner

*Primary Examiner* — Qiuwen Mi
(74) *Attorney, Agent, or Firm* — Dentons US LLP

(57) ABSTRACT

Compositions for lubricating skin during application of a fascia tissue treatment device, thereby reducing the appearance of cellulite in skin and methods of forming such compositions.

12 Claims, No Drawings

COMPOSITIONS FOR USE WITH A FASCIA TISSUE TREATMENT DEVICE TO REDUCE CELLULITE

FIELD OF THE INVENTION

The principles of the present invention relate generally to compositions, and methods of forming such compositions, for topical application to the skin which comprise various plant extracts and the use of such compositions to provide benefits to the skin, in particular, lubrication for fascial release with a fascia tissue treatment device producing aesthetic improvement and/or anti-cellulite benefits.

BACKGROUND OF THE INVENTION

Fascia is a layer of fibrous connective tissue beneath the skin that attaches, stabilizes, encloses, separates muscles and other internal organs, and performs other functions. The tissue allows for proper functioning of muscles with respect to one another and nerve communications, among other dynamic operations. When fascia tissue becomes damaged by injury, tissue knots, or other medical reasons, it can take time to correct itself. Alternatively, fascia distortions of all types can be repaired by direct manipulation, such as fascial release and/or therapy, to allow for proper functioning of the tissue and allow the underlying muscle as well as other bodily functions to properly operate. In some cases, damaged fascia can be repaired without much difficulty, while in other cases, restoring fascia to its proper form can take considerably more effort. Other reasons for treating fascia include cosmetic reasons, including people who have dimpled skin, fatty, saggy skin, and circulatory problems, for example. Fascia, when properly treated, can considerably reduce the dimples in skin caused by cellulite, as well as many other cosmetic benefits to the skin and shape of the body.

Cellulite is the herniation of subcutaneous fat within fibrous connective tissue that manifests topographically as skin dimpling and nodularity, often, but not limited to, in the buttocks, thighs, and abdomen. Excess fat accumulation increases the volume of adipocytes, which bulge into a weakened dermis to create the characteristic irregularities in the appearance of the epidermal surface. A number of factors can cause cellulite including, for example, genetics, hormones, and lifestyle. Dieting to decrease fat intake, exercising to increase fat metabolism and prevent the build up of cellulite, and fascial release and hydrotherapy to stimulate lymphatic drainage can help reduce the appearance of cellulite. However, these means for combating cellulite or subcutaneous fat are limited, and the need remains for additional approaches. The protrusion of enlarged fat tissue into the dermis is one of the major factors contributing to the appearance of cellulite. One of the approaches to reduce cellulite is to stimulate fat breakdown and reduce the amount of fat and/or lipids in the adipocytes, or fat cells. There is active interest in the cosmetics industry in developing products that may be applied topically to the skin to counteract adverse changes in the skin, such as cellulite, saggy skin, fatty and uneven texture. As a result, cosmetic products that reverse or forestall such changes are increasingly in demand. Consumers continually seek to improve the appearance of skin affected by unwanted deposition and/or accumulation of fat, including cellulite and other issues.

BRIEF SUMMARY OF THE INVENTION

In combination, a fascia tissue treatment device lubricated with an oil composition to reduce cellulite can significantly improve skin aesthetic appearance and would be advantageous in the formulation of treatments, products, and protocols for the skin. As described herein, innovative and useful compositions for use as a lubricant with a fascia tissue treatment device for the treatment of cellulite and the like are provided along with methods for forming such compositions.

One aspect of the present disclosure is the provision of compositions for reducing cellulite and lubricating skin during treatment with a fascia tissue treatment device. In one embodiment, the composition comprises sunflower seed oil. In another embodiment, the composition comprises caprylic/capric triglyceride. In yet another embodiment, the composition comprises rice bran extract. In still another embodiment, the composition comprises plankton extract. In other embodiments, the composition comprises rosemary leaf extract. In yet other embodiments, the composition comprises sunflower extract. In some embodiments, the composition comprises tocopherol. In particular embodiments, the composition comprises isopropyl myristate. In certain embodiments, the composition comprises soybean seed oil. In one embodiment, the composition comprises lavender oil. In another embodiment, the composition comprises lavendin oil. In yet another embodiment, the composition comprises phenoxyethanol. In still another embodiment, the composition comprises caprylyl glycol. In other embodiments, the composition comprises ethylhexylglycerin. In yet other embodiments, the composition comprises hexylene glycol. In some embodiments, the composition comprises fragrance.

In certain embodiments, the sunflower seed oil, sunflower extract, or both are from *Helianthus annuus*. In one embodiment, the rice bran extract is from *Oryza sativa*. In another embodiment, the rosemary leaf extract is from *Rosmarinus officinalis*. In still another embodiment, the soybean seen oil is from *Glycine soja*. In other embodiments, the lavender oil is from *Lavandula angustifolia*. In some embodiments, the lavendin oil is from *Lavandula* hydrida.

In particular embodiments, the seed oil can be from about 80%, about 81%, about 82%, about 83%, about 84%, about 85%, about 86%, about 87%, about 88%, about 89%, about 90%, about 91%, about 92%, about 93%, about 94%, or about 95% of the total weight by volume of the composition. In certain embodiments, the caprylic/capric triglyceride can be from about 5.0%, about 5.5%, about 6.0%, about 6.5%, about 7.0%, about 7.5%, about 8.0%, about 8.5%, about 9.0%, about 9.5%, or about 10.0% of the total weight by volume of the composition. In one embodiment, the rice bran extract can be from about 1.0%, about 1.5%, about 2.0%, about 2.5%, about 3.0%, about 3.5%, or about 4.0% of the total weight by volume of the composition. In another embodiment, the plankton extract can be from about 0.01%, about 0.02%, about 0.03%, about 0.04%, about 0.05%, about 0.06%, about 0.07%, about 0.08%, or about 0.09% of the total weight by volume of the composition. In yet another embodiment, the rosemary leaf extract can be from about 0.01%, about 0.02%, about 0.03%, about 0.04%, about 0.05%, about 0.06%, about 0.07%, about 0.08%, or about 0.09% of the total weight by volume of the composition. In still another embodiment, the sunflower extract can be from about 0.1%, about 0.2%, about 0.3%, about 0.4%, about 0.5%, about 0.6%, about 0.7%, about 0.8%, or about 0.9% of the total weight by volume of the composition. In other embodiments, the tocopherol can be from about 0.01%, about 0.02%, about 0.03%, about 0.04%, about 0.05%, about 0.06%, about 0.07%, about 0.08%, or about 0.09% of the total weight by volume of the composition. In yet other embodiments, the isopropyl myristate can be from about 0.1%, about 0.2%, about 0.3%, about 0.4%, about 0.5%, about 0.6%, about 0.7%, about 0.8%, or about 0.9% of the total weight by volume of the composition. In some embodiments, the soybean seed oil can be from about 0.1%, about 0.2%, about 0.3%, about 0.4%, about 0.5%, about 0.6%, about 0.7%, about 0.8%, or about 0.9% of the total weight by volume of the composition. In particular embodiments, the lavender oil can be from about 0.01%, about 0.02%, about 0.03%, about 0.04%, about 0.05%, about 0.06%, about 0.07%, about 0.08%, or about 0.09% of the total weight by volume of the composition. In certain embodiments, the lavendin oil can be from about 0.01%, about 0.02%, about 0.03%, about 0.04%, about 0.05%, about 0.06%, about 0.07%, about 0.08%, or about 0.09% of the total weight by volume of the composition. In one embodiment, the phenoxyethanol can be from about 0.1%, about 0.2%, about 0.3%, about 0.4%, about 0.5%, about 0.6%, about 0.7%, about 0.8%, or about 0.9% of the total weight by volume of the composition. In another embodiment, the caprylyl glycol can be from about 0.1%, about 0.2%, about 0.3%, about 0.4%, about 0.5%, about 0.6%, about 0.7%, about 0.8%, or about 0.9% of the total weight by volume of the composition. In yet another embodiment, the ethylhexylglycerin can be from about 0.01%, about 0.02%, about 0.03%, about 0.04%, about 0.05%, about 0.06%, about 0.07%, about 0.08%, or about 0.09% of the total weight by volume of the composition. In still another embodiment, the hexylene glycol can be from about 0.01%, about 0.02%, about 0.03%, about 0.04%, about 0.05%, about 0.06%, about 0.07%, about 0.08%, or about 0.09% of the total weight by volume of the composition. In other embodiments, the fragrance can be from about 0.1%, about 0.2%, about 0.3%, about 0.4%, about 0.5%, about 0.6%, about 0.7%, about 0.8%, or about 0.9% of the total weight by volume of the composition. Comparable percentages may be provided for by volume of the total composition. A person of ordinary skill in the art would understand that the concentrations can vary depending on the addition, substitution, and/or subtraction of ingredients in a given composition.

In some embodiments, the composition can be stored in a dispenser for spray or other dispensing method. In one embodiment, the dispenser can be integrated into or onto the fascia tissue treatment device. Alternatively, the dispenser may be external from the fascia tissue treatment device. In an alternative embodiment, the dispenser can include a member that functions to dispense the composition in a roll-on, sponge applicator, spray squirt device, or other dispensing technique. A cartridge that includes the composition can be used and positioned within a dispensing mechanism of the fascia tissue treatment device. In particular embodiments, the composition can be applied from a dispenser. In certain embodiments, the dispenser comprises a spray mechanism.

Another aspect of the present disclosure is the provision of a method of forming a composition for reducing cellulite and other skin discrepancies, such as fat pockets, skin texture, spider veins, varicose veins, poor circulation and related issues, rashes, and lubricating skin during treatment with a fascia tissue treatment device. In one embodiment, the method comprises mixing sunflower seed oil, caprylic/capric triglyceride, rice bran extract, plankton extract, rosemary leaf extract, sunflower extract, tocopherol, isopropyl myristate, soybean seed oil, lavender oil, lavendin oil, phenoxyethanol, caprylyl glycol, ethylhexylglycerin, hexylene glycol, fragrance, or any combination thereof.

DETAILED DESCRIPTION OF THE INVENTION

A combination of ingredients have been found to synergistically reduce cellulite and improve other beauty conditions over a period of time. Treatment with a fascia tissue treatment device can produce better results of certain conditions, such as, but not limited to, reducing subcutaneous fat by utilizing the combination of ingredients. A fascia tissue treatment device, as described in U.S. Patent Application No. 2014/0243718, can include a bar and a plurality of flower-like or claw-shaped element(s) connected to the bar along a plane. The flower-like elements can each include multiple fingers that are stiff and extend outward from the bar. Without being bound by theory, it is believed that at least one of the ingredients in the oil described herein work to induce thermogenic processes in the body for cellulite and fat reducing effects during application and use of fascia tissue treatment device. In particular, the oil composition may increase (3-oxidation of fatty acids in adipocytes, thereby burning accumulated fat. A dermatologically acceptable vehicle was discovered that provides a stable environment for the active ingredients while also providing lubrication for the fascia tissue treatment device, and a pleasant scent and tactile property when applied to skin. Because the use of the fascia tissue treatment device can occur after showering, for example, the pleasant scent avoids a common resistance of users of certain ingredients that provide for burning accumulated subcutaneous fat due to unpleasant odors.

The principles described herein relate to compositions for reducing cellulite and affecting of the beauty conditions and body fat while both lubricating skin for application of a fascia tissue treatment device and having a pleasant odor. In one embodiment, the composition includes the active ingredients caprylic/capric triglyceride, plankton extract, and tocopherol. One source of such active ingredients is, for example, Lipout™ by Provital Group, Barcelona, Spain. Lipout is microalgae, *Tisochrysis lutea*, which is standardized for xanthophylls and rich in polyunsaturated fatty acids. Lipout may be used to activate a browning function of adipocytes to sculpt the body and to reduce cellulite appearance with improved firmness and elasticity. In particular embodiments, to provide a satisfying and pleasant aroma in addition to adequate lubrication for use with a fascia tissue treatment device, the composition includes additional compounds in conjunction with active ingredients. In some embodiments, the composition includes sunflower seed oil, caprylic/capric triglyceride, rice bran extract, plankton extract, rosemary leaf extract, sunflower extract, tocopherol, isopropyl myristate, soybean seed oil, lavender oil, lavendin oil, phenoxyethanol, caprylyl glycol, ethylhexylglycerin, hexylene glycol, fragrance, or any combination thereof. The compositions can include any number of combinations of additional ingredients described throughout this specification. The concentrations of the any ingredient within the compositions can vary. In non-limiting embodiments, for example, the compositions can comprise, consisting essentially of, or consist of, in their final form, for example, about 0.01% to about 95.00% or any range derivable therein, of at least one of the ingredients that are mentioned throughout the specification and claims. The percentage can be calculated by weight of the total composition. A person of ordinary skill in the art would understand that the concentrations can vary depending on the addition, substitution, and/or subtraction of ingredients in a given composition.

The disclosed compositions can also include various antioxidants to retard oxidation of one or more components. Additionally, the prevention of the action of microorganisms can be brought about by preservatives, such as various antibacterial and antifungal agents. Further, the disclosed compositions can also include cosmetic ingredients, UV absorption agents, moisturizing agents, structuring agents, emulsifiers, thickening agents, and pharmaceutical ingredients.

The disclosed compositions can be incorporated into all types of formulations. Non-limiting examples of suitable formulations include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydroalcoholic), anhydrous bases (such as lipsticks and powders), gels, and ointments or by other method or any combination of the forgoing as would be known to one of ordinary skill in the art. Variations and other appropriate formulations will be apparent to the skilled artisan and are appropriate for use in the present embodiment. In certain embodiments, it is important that the concentrations and combinations of the compounds, ingredients, and agents be selected in such a way that the combinations are chemically compatible and do not form complexes which precipitate from the finished product.

It is also contemplated that ingredients identified throughout this specification, including but not limited to caprylic/capric triglyceride, plankton extract, and tocopherol, or any combinations thereof, can be individually or combinatorially encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed) that can be used as delivery vehicles to deliver the ingredient to skin. See, e.g., U.S. Pat. Nos. 6,387,398; 6,203,802; and 5,411,744.

The principles described herein also relate to a process of forming a composition to reduce cellulite and lubricate the skin for application of a fascia tissue treatment device. In certain embodiments, the process includes mixing sunflower seed oil, caprylic/capric triglyceride, rice bran extract, plankton extract, rosemary leaf extract, sunflower extract, tocopherol, isopropyl myristate, soybean seed oil, lavender oil, lavendin oil, phenoxyethanol, caprylyl glycol, ethylhexylglycerin, hexylene glycol, fragrance, or any combination thereof.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Compounds

Body fat, cellulite, and other beauty conditions can be reduced by triggering the thermogenic processes within adipocytes using the active ingredients caprylic/capric triglyceride, plankton extract, and tocopherol optionally in conjunction with the application of a fascia tissue treatment device. A composition comprising sunflower seed oil, caprylic/capric triglyceride, rice bran extract, plankton extract, rosemary leaf extract, sunflower extract, tocopherol, isopropyl myristate, soybean seed oil, lavender oil, lavendin oil, phenoxyethanol, caprylyl glycol, ethylhexylglycerin, hexylene glycol, and fragrance can visibly reduce the unsightly effects of cellulite on the skin following repeated topical applications during use of a fascia tissue treatment device.

The composition can include:

| INCI Name | Percent (wt/vol %) |
| --- | --- |
| *Helianthus annuus* seed oil | 80.0-95.0 |
| caprylic/capric triglyceride | 5.0-10.0 |
| *Oryza sativa* bran extract | 1.0-4.0 |
| plankton extract | 0.01-0.09 |
| *Rosmarinus officinalis* leaf extract | 0.01-0.09 |
| *Helianthus annuus* extract | 0.1-0.9 |
| Tocopherol | 0.01-0.09 |
| isopropyl myristate | 0.1-0.9 |
| *Glycine soja* seed oil | 0.1-0.9 |
| *Lavandula angustifolia* oil | 0.01-0.09 |
| *Lavandula hybrida* oil | 0.01-0.09 |
| Phenoxyethanol | 0.1-0.9 |
| caprylyl glycol | 0.1-0.9 |
| Ethylexylglycerin | 0.01-0.09 |
| hexylene glycol | 0.01-0.09 |
| Fragrance | 0.1-0.9 |
| Total | 100.00 |

Example 2: Compound Preparation

To prepare a dermatologically acceptable vehicle that provides a chemically stable and cosmetically acceptable environment for the ingredients capable of reducing cellulite, impacting other beauty conditions, and lubricating the skin during an optional usage or application of a fascia tissue treatment device, caprylic/capric triglyceride, plankton extract, and tocopherol can be mixed with sunflower seed oil, rice bran extract, rosemary leaf extract, sunflower extract, isopropyl myristate, soybean seed oil, lavender oil, lavendin oil, phenoxyethanol, caprylyl glycol, ethylhexylglycerin, hexylene glycol, and fragrance.

The amount of each ingredient can vary. For example, the composition can include sunflower seed oil from about 80.0% to about 95.0%; caprylic/capric triglyceride from about 5.0% to about 10.0%; rice bran extract from about 1.0% to about 4.0%; plankton extract from about 0.01% to about 0.09%; rosemary leaf extract from about 0.01% to about 0.09%; sunflower extract from about 0.1% to about 0.9%; tocopherol from about 0.01% to about 0.09%; isopropyl myristate from about 0.1% to about 0.9%; soybean seed oil from about 0.1% to about 0.9%; lavender oil from about 0.01% to about 0.09%; lavendin oil from about 0.01% to about 0.09%; phenoxyethanol from about 0.1% to about 0.9%; caprylyl glycol from about 0.1% to about 0.9%; ethylhexylglycerin from about 0.01% to about 0.09%; hexylene glycol from about 0.01% to about 0.09%; and fragrance from about 0.1% to about 0.9% of the total weight by volume, of the entire composition.

As various modifications could be made in the compositions and methods herein described without departing from the scope of the invention, it is intended that all matter contained in the foregoing description shall be interpreted as illustrative rather than limiting. The breadth and scope of the present invention should not be limited by any of the above-described exemplary embodiments, but should be defined only in accordance with the following claims appended hereto and their equivalents. All patent and non-patent documents cited in this specification are incorporated herein by reference in their entireties.

What is claimed:

1. A composition comprising sunflower seed oil, caprylic/capric triglyceride, rice bran extract, plankton extract, rosemary leaf extract, sunflower extract, tocopherol, isopropyl myristate, soybean seed oil, lavender oil, lavendin oil, phenoxyethanol, caprylyl glycol, ethylhexylglycerin, hexylene glycol, and fragrance, further wherein the sunflower seed oil is from about 80% to about 95.0%, the caprylic/capric triglyceride is from about 5.0% to about 10.0%, the rice bran extract is from about 1.0% to about 4.0%, the plankton extract is from about 0.01% to about 0.09%, the rosemary leaf extract is from about 0.01% to about 0.09%, the sunflower extract is from about 0.1% to about 0.9%, the tocopherol is from about 0.01% to about 0.09%, the isopropyl myristate is from about 0.1% to about 0.9%, the soybean seed oil is from about 0.1% to about 0.9%, the lavender oil is from about 0.01% to about 0.09%, the lavendin oil is from about 0.01% to about 0.09%, the phenoxyethanol is from about 0.1% to about 0.9%, the caprylyl glycol is from about 0.1% to about 0.9%, the ethylhexylglycerin is from about 0.01% to about 0.09%, the hexylene glycol is from about 0.01% to about 0.09%, and the fragrance is from about 0.1% to about 0.9% of the total weight by volume of the composition.

2. The composition according to claim 1, wherein the sunflower seed oil, sunflower extract, or both, are from *Helianthus annuus*.

3. The composition according to claim 1, wherein the rice bran extract is from *Oryza sativa*.

4. The composition according to claim 1, wherein the rosemary leaf extract is from *Rosmarinus officinalis*.

5. The composition according to claim 1, wherein the soybean seen oil is from *Glycine soja*.

6. The composition according to claim 1, wherein the lavender oil is from *Lavandula angustifolia*.

7. The composition according to claim 1, wherein the lavendin oil is from *Lavandula hybrida*.

8. The composition according to claim 1, wherein the composition is in the form of an emulsion.

9. The composition according to claim 1, wherein the composition is in the form of a cream.

10. The composition according to claim 1, wherein the composition is in the form of a lotion.

11. The composition according to claim 1, wherein the composition is in the form of a gel.

12. The composition according to claim 1, wherein the composition is in the form of an ointment.

* * * * *